United States Patent [19]

Ura et al.

[11] Patent Number: 5,382,517
[45] Date of Patent: Jan. 17, 1995

[54] PROCESS FOR THE PREPARATION OF L-SERINE BY AN ENZYMATIC METHOD

[75] Inventors: Daisuke Ura; Tadashi Hashimukai; Toshio Matsumoto; Nobuhiro Fukuhara, all of Fukuoka, Japan

[73] Assignee: Mitsui Toatsu Chemicals, Inc., Tokyo, Japan

[21] Appl. No.: 20,446

[22] Filed: Feb. 22, 1993

Related U.S. Application Data

[63] Continuation of Ser. No. 592,508, Oct. 3, 1990, abandoned.

[30] Foreign Application Priority Data

Oct. 6, 1989 [JP] Japan ................... 1-260203

[51] Int. Cl.$^6$ .............................................. C12P 13/06
[52] U.S. Cl. ................................... 435/116; 435/193; 435/232; 435/106
[58] Field of Search ................ 435/116, 193, 232, 106

[56] References Cited

U.S. PATENT DOCUMENTS 4,782,021 11/1988 Ishiwata et al. ................... 435/116

FOREIGN PATENT DOCUMENTS 0185824 7/1986 European Pat. Off. ............ 435/116

OTHER PUBLICATIONS

Chemical Abstracts 107:234706q "Efficient conversion of glycine to L-serine by a glycine-resistant mutant of a methylotroph using cobalt(2+) as an inhibitor of L-serine degradation".
Patent Abstracts of Japan, vol. 7, No. 242 (Oct. 27, 1983) "Method for Suppressing Activity of Serine Decomposing Enzyme in Bacterial Cell".

Primary Examiner—Marian Knode
Attorney, Agent, or Firm—Burns, Doane, Swecker & Mathis

[57] ABSTRACT

The invention relates to a process for preparing L-serine from glycine and formaldehyde in the presence of cells of a microorganism or a cell-treated product having a serine hydroxymethyl transferase activity by an enzymatic method.

13 Claims, 1 Drawing Sheet

PROCESS FOR THE PREPARATION OF L-SERINE BY AN ENZYMATIC METHOD

RELATED APPLICATIONS

This application is a continuation of U.S. Ser. No. 07/592,508, filed Oct. 3, 1990, now abandoned.

BACKGROUND OF THE INVENTION

1. Field of The Invention

This invention relates to a process for preparing L-serine and more particularly, to a process for preparing L-serine from glycine and formaldehyde in the presence of cells of a microorganism or cell-treated product having a serine hydroxymethyl transferase activity by an enzymatic method.

2. Description of the Prior Art

L-Serine is an amino acid which is utilized as medicines, cosmetics and starting materials for chemicals and has now been prepared by chemical synthetic processes or enzymatic processes using glycine as a precursor.

However, the chemical synthetic processes inevitably involve formation of a DL product, with an attendant disadvantage that for the preparation of an L product alone, optical resolution has to be used. On the other hand, the enzymatic process using glycine as a precursor is disadvantageous in the quantity of accumulation, yield, purification and treatment of waste water. Thus, these known processes are not always practically useful processes.

In place of these processes, attention has been recently paid to a process wherein L-serine is enzymatically prepared from glycine and formaldehyde by utilizing serine hydroxymethyl transferase (EC 2.1.2.1, hereinafter referred to as "SHMT").

Moreover, since there is known a process wherein the SHMT activity of microorganisms is improved by gene engineering (*Gene*, 14, p, 63–72 (1981), *Gene* 27, p.47 54 (1984)), processes utilizing SHMT obtained from microorganisms are expected to be more industrially advantageous in the future.

As an industrial process of conveniently producing L-serine from glycine and formaldehyde according to an enzymatic process utilizing SHMT, there is known a process wherein microorganisms or their cells having SHMT activity are contacted with a glycine solution and are subsequently used for the reaction with L-serine (Japanese Laid-open Application No. 61-9294). However, it is known that microorganism have a serine decomposition enzymatic activity (hereinafter referred to as SD activity) (for example, L-serine dehydratase as described in (1) Shizuta Y. and Tokushige M, *Methods In Enzymology* 17B, p. 575–580, Academic Press Inc. New York (1971), (2) Burns. R. O. *Methods In Enzymology* 17B, Academic Press, New York (1971), and (3) Kubota. K. et al, *J. Fermentation and Bioengineering* 67, (6), p. 391–394 (1988)).

The SD activity presents the following problems in the process for preparing L-serine by the enzymatic method.

(1) Because of the decomposition of produced L-serine, the yield (based on starting glycine) decreases.

(2) The L-serine formation reaction is suppressed by means of the decomposition product of L-serine with a decrease in the amount of accumulated or precipitated serine.

To avoid the above, there is known a process for efficiently producing L-serine by the use of a variant strain of microorganisms wherein the SD activity is reduced. [literature ((1) Kubota K. *Agric. Biol. Chem.* 49, p. 7–12 (1985)]. However, it is not easy to obtain SD-deactivated variant strains and the appearance of the denatured strains is a problem. Thus, such a process is disadvantageous as a process on an industrial scale.

The suppression of the serine decomposition activity is disclosed in Japanese Laid-open Patent Application Nos. 58-129972 and 58-129975. However, in either application, the bacteria are treated at a specific temperature of 40° to 60° C. within a short time of 10 to 30 minutes. Since the treating time is short, the serine dehydration activity will not be completely deactivated.

SUMMARY OF THE INVENTION

It is an object of the invention to provide a process for preparing L-serine from glycine and formaldehyde which overcomes the disadvantages of the prior art processes.

It is another object of the invention to provide a process for preparing L-serine from glycine and formaldehyde by the use of a cell-treated product of a microorganism which has not only the SHMT activity, but also the SD activity wherein the SD activity present in the cells or cell-treated product is selectively lowered while suppressing the lowering of the SHMT activity.

We have made intensive studies on a process for preparing L-serine in the presence of cells of a microorganism having SHMT enzymatic activity or a cell-treated product. As a result, it has been found that when a suspension of microorganism cells having not only SHMT activity but also SD activity or a solution of a cell-treated product is pre-treated at a temperature of not higher than 60° C. under conditions where dissolved oxygen is present at a level of not lower than 1 ppm, the SD activity can be selectively lowered. The use of the thus pretreated microorganism cells or cell-treated product ensures efficient preparation of L-serine from glycine and formaldehyde.

In order to achieve the objects of the invention, there is provided a process for preparing L-serine from glycine and formaldehyde in the presence of microorganism cells or a cell-treated product having an enzymatic serine hydroxymethyl transferase activity, the process characterized in that a suspension of the cells or a solution of the cell-treated product is pretreated at a temperature of not higher than 60° C. by passing oxygen or air in the suspension or solution so that a concentration of dissolved oxygen is maintained at a level of not lower Than 1 ppm and the resultant microorganism cells or cell-treated product having the enzymatic activity is used for the preparation of L-serine.

DESCRIPTION OF THE PREFERRED EMBODIMENTS OF THE INVENTION

Figure 1:
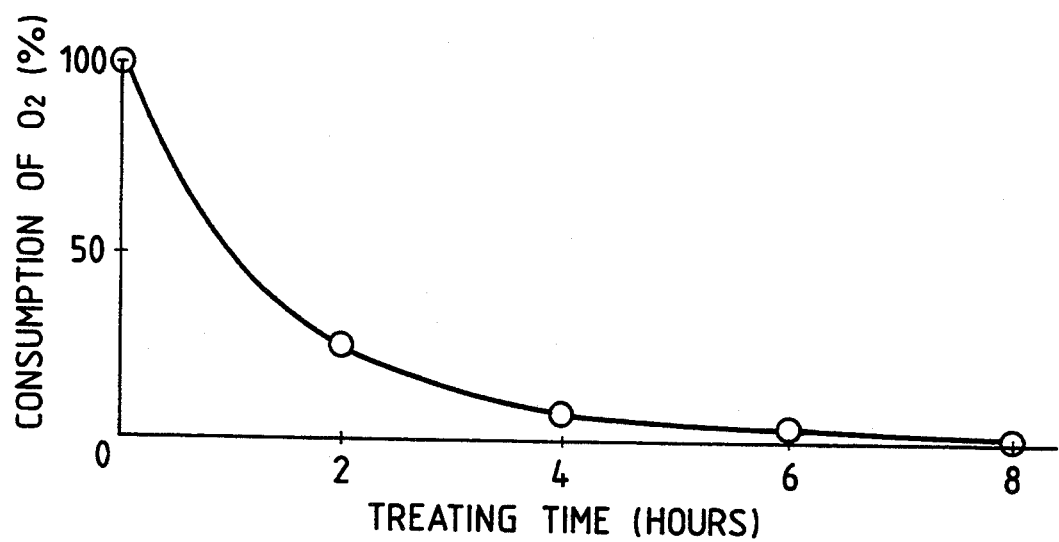
FIG. 1 is a graphical representation of the consumption of $O_2$ in relation to the variation in treating time.

The microorganisms used in the practice of the invention are not critical provided that they have SHMT activity. Specific examples of the microorganisms include *Escherichia coli* MT-10350 (FERM P-7437: FERM BP-793) and *Escherichia coli* MT-10351 (FERM P-7438: FERM BP-749). These microorgansims have been deposited under the Budapest Treaty at the Fermentation Research Institute, 1-3, Higashi 1 chome, Tsukaba-shi, Ibaraki-ken 305, Japan on Feb. 4, 1984.

For the culture of microorganisms used in the present invention, any known synthetic media and natural media containing carbon sources, nitrogen sources, inorganic salts, organic nutrients and the like which can be used by the strain used may be employed. In general, the culture is aerobically carried out at a temperature of from 25° to 40° C. at a pH of the culture solution of from 6 to 8.

In the practice of the invention, the culture medium obtained in this manner is subjected to centrifugal separation or filtration to collect cells or a cell-treated product for use as an enzymatic source. The cell-treated product may be obtained by mechanical disruption, an ultrasonic disintegration, a freezing-thawing treatment, a drying treatment, a solvent treatment, a chemical treatment, an osmotic treatment, self-digestion, a treatment with surface active agents, or an enzymatic treatment of the cells, thereby obtaining pieces where cell walls are partially or wholly broken, an enzyme fraction containing the pieces, and immobilized products of the cells and a cell extract.

The cells should preferably be separated from the culture medium wherein the carbon source, e.g., glucose, has been consumed.

In the practice of the invention, while the cells or cell treated product used in the present invention is maintained at a temperature of not higher than 60° C., preferably from 30° to 50° C., oxygen or air is passed thereinto or agitation is continued so that the concentration of dissolved oxygen in a treating solution should invariably be at a level of not less than 1 ppm. By this, the SD activity alone in the cells or the cell treated product can be selectively lowered.

If the treating temperature is lower than 30° C., there is the tendency that the SD activity cannot be suppressed. Over 60° C., not only the SD activity, but also the SHMT activity is unfavorably lowered.

The amount of the dissolved oxygen in the treating solution may vary depending on the type of solute and is satisfactory when the dissolved oxygen is present at a level of not less than 1 ppm in the treating solution. The pH of the treating solution is generally in the range of from 6 to 9, and the treating time is generally in the range of from 2 to 10 hours, preferably from 4 to 8 hours.

During the deactivation treatment of the SD activity, any anti-foaming agent ordinarily used for this purpose may be used in order to prevent foaming. Preferably, glycine may be added to the treating solution. The cells or cell treated product having the SHMT activity which has been pretreated is used to carry out the preparation of L-serine.

The synthetic reaction of L-serine according to the invention should preferably be effected at a pH of from 6 to 9 at a temperature of from 30° to 60° C. under agitation. Because the enzyme, SHMT, requires tetrahydrofolic acid and pyridoxal phosphate as coenzymes, the addition of these cofactors to the reaction system may facilitate the L-serine reaction. It will be noted that the L-serine reaction of the invention may be conducted in an atmosphere of nitrogen or in the presence of a reducing agent.

The amount of glycine used as the reaction substrate may be not less than the saturated solubility at the reaction temperature and should preferably be a concentration of about 5M. Glycine may be added at one time at the time of commencing the reaction, or may be added portion by portion as the reaction proceeds.

Formaldehyde which is the other reaction substrate may be used in the form of a gas, an aqueous solution, an alcoholic solution or a solid polymerized product of paraformaldehyde. Preferably, formalin which is an aqueous solution having a concentration of about 37 to 43% is used.

Formaldehyde should be used at a concentration not impeding the SHMT enzymatic activity and is added to the reaction solution portion by portion or continuously as the reaction proceeds.

The L-serine preparation reaction in accordance with the method of the invention is effected generally at a pH of from 6 to 9 at a reaction temperature of from 30° to 60° C. for a reaction time of from 5 to 40 hours, and preferably at a reaction temperature of from 40° to 50° C. for a time of 20 to 30 hours.

The adjustment of pH is carried out by addition of an alkali to the reaction system. Examples of the alkali added to the reaction system include alkali metal hydroxides such as lithium hydroxide, sodium hydroxide, potassium hydroxide and the like, along with other compounds capable of being dissolved in water and exhibiting basicity, e.g. potassium pyrophosphate, ammonia and the like.

How the reaction proceeds can be confirmed by analysis of concentrations of L-serine and glycine in the reaction solution by liquid chromatography.

The after-treatment of the reaction solution after completion of the reaction is to add mineral acids such as sulfuric acid, hydrochloric acid or the like to the reaction solution to make the pH acidic, preferably, at a pH of 5 or below for dissolution of the L-serine To the solution is added a filtration aid, for example, active carbon, followed by thermal filtration to remove cell debris therefrom.

The filtrate is concentrated by a known method to precipitate crystals of L-serine, followed by separation and drying to obtain L-serine.

As will be apparent from the above description, the features of the invention reside in the lowering of the SD activity by which the L-serine preparation reaction can proceed with the following advantages.

(1) The decomposition of produced L-serine can be suppressed with an improved reaction yield (based on the starting glycine).
(2) The suppression of the L-serine formation reaction by means of a L-serine decomposition product with a lowering in amount of accumulation of serine is prevented, The present invention is described in more detail by way of examples and experimental examples, which should not be construed as limiting the invention.

Experimental Example 1

The strain of *Escherichia coli* MT-10350 (FERM P-7437) was implanted in an LB-AP agar plate medium described hereinafter and cultured overnight at 35° C. Two platinum loops from the resultant colonies were inoculated in a 500 ml Sakaguchi's shoulder flask provided with a cotton stopper in which a 150 ml LB-AP liquid medium was placed. The inoculated Sakaguchi's shoulder flask was subjected to shaking culture (120 rpm) at 35° C. for 20 hours, After being cultured for the given time, the liquid medium was transferred to a 30 liters jar fermenter in which 20 liters of a PT minimum medium was charged, followed by culturing for 40 hours at 35° C. at an aeration amount of 1 vvm at a frequency number of 600 r.p.m. while controlling the pH to 6.8 by addition of an aqueous ammonia solution and adding a sterilized 40% glucose aqueous solution portion by portion.

After the cultivation for the given time and confirmation of the consumption of the glucose in the medium, the cells were immediately harvested by centrifugation. 0.46 kg of the thus-obtained wet cells was added to a solution of 1.43 kg of water and 0.41 kg of glycine. The pH was adjusted to 7.5 by the use of NaOH and the solution was maintained at 40° C. for 16 hours under agitation.

After the reaction for the given time, the reaction mixture was diluted 1:2 with distilled water for determination of SD activity and SHMT activity, followed by addition of an anti-foaming agent (Adekanol® LG-109, available from Asahi Denka Co., Ltd.) in a concentration of 0.1%, and the aeration was controlled to keep the respective concentrations of dissolved oxygen in Table 1. Two hours and four hours after the aeration, the residual SD activity and SHMT activity were, respectively, determined.

TABLE 1

Concentration of dissolved oxygen at the time of deactivation treatment and residual rates of the SD and SHMT activities

| Residual Rate | Dissolved Oxygen (ppm) | | | | | |
|---|---|---|---|---|---|---|
| | 0 | | 1 | | 6 | |
| | SD | SHMT | SD | SHMT | SD | SHMT |
| | ← | ← | ← | ← | ← | ← |
| Aeration Time | | | | | | |
| 0 hour | 100(%) | 100(%) | 100(%) | 100(%) | 100(%) | 100(%) |
| 2 hours | 100 | 98 | 30 | 98 | 10 | 98 |
| 4 hours | 100 | 98 | 10 | 98 | 5 | 98 |

Medium Composition

| 1. LB-AP agar plate medium | |
|---|---|
| Bacto ® Tryptone(Difco Inc.) | 10.0 g |
| Bacto ® Yeast extract (Difco Inc.) | 5.0 g |
| NaCl | 10.0 g |
| distilled water | 1000 ml |
| pH = 7.5 adjusted with NaOH | |

After the pH adjustment, 15 g of agar was added, and was sterilized in an autoclave (120° C.,) 10 minutes) and cooled down to 60° C., followed by addition of ampicillin at a concentration of 25 μg/liter through a sterile filter and placement in a Petri dish wherein it was solidified to obtain an agar plate.

2. LB-AP Liquid Medium

| 2. LB-AP liquid medium | |
|---|---|
| Bacto ® Tryptone(Difco Inc.) | 10.0 g |
| Bacto ® Yeast extract (Difco Inc.) | 5.0 g |
| NaCl | 10.0 g |
| distilled water | 1000 ml |
| pH = 7.5 adjusted with NaOH | |

After the pH adjustment, the mixture was sterilized in an autoclave (120° C., 10 minutes) and cooled down to 60° C., followed by addition of ampicillin through a sterile filter at a concentration of 25 μg/liter.

3. PT Minimum Medium

| 3. PT minimum medium | |
|---|---|
| potassium phosphate monobasic | 2.0 g |
| potassium phosphate dibasic | 2.0 g |
| $MgSO_4.7H_2O$ | 2.0 g |
| $(NH_4)_2SO_4$ | 1.5 g |
| L-phenylalanine | 2.5 g |
| $CaCl_2.2H_2O$ | 80 mg |
| $CuCl_2.2H_2O$ | 8 mg |
| $CoCl_2.6H_2O$ | 8 mg |
| $AlCl_3.6H_2O$ | 8 mg |
| $H_3BO_3$ | 1 mg |
| $MnSO_4.5H_2O$ | 20 mg |
| $ZnSO_4.7H_2O$ | 4 mg |
| $Na_2MoO_4.2H_2O$ | 4 mg |
| $FeSO_4.7H_2O$ | 80 mg |
| distilled water | 1000 ml |

The above ingredients were mixed and sterilized at 120° C. for 30 minutes, followed by addition of a hydrochloric acid thiamine aqueous solution sterilized through a 0.2 μm sterile filter at a thiamine concentration of 50 mg/liter.

Measurement of The SD Activity and SHMT Activity

1. Measurement of the SD Activity 0.1 ml of a 500 mM phosphate buffer solution (pH 7.5), 0.6 ml of a 33 mM L-serine aqueous solution, 0.1 ml of pyridoxal phosphate (50 mM phosphate buffer solution (pH 7.5)) and 0.1 ml of distilled water were placed in a 2.2 ml Eppendorf tube for pre-incubation at 30° C. for 5 minutes. Next, 0.4 ml of the cell-treated solution was added to the solution and agitated, followed by reaction at 30° C. for 2 hours after completion of the reaction for a certain time, after which 0.2 ml of trichloroacetic acid (15% aqueous solution) was added thereby stopping the reaction. The reaction solution was centrifugally separated and the resultant supernatant liquid was diluted to 1:10, followed by liquid chromatography (hereinafter referred to as HPLC) to analyze L-serine. For control, after the pre-incubation, trichloroacetic acid was added to the reaction solution, followed by addition of the cell-treated solution. The reaction was performed for a predetermined time at 30° C., followed by centrifugal separation in the same manner as described above to determine the concentration of L-serine in the supernatant liquid for use as a reference. The analyzing conditions of serine by HPLC were as follows.

HPLC analysis conditions (quantitative determination of L-serine and glycine)

The mobile phase of distilled water was degassed and the flow rate was set at 1.0 ml/minute. The analysis was made according to a post labelling method. More particularly, a color developer was 0.08% o-phthalaldehyde in 2% KOH solution which was passed at a flow rate of 0.4 ml/minute. The detector used was a fluorescent detector using an irradiation wavelength of 365 nm and a radiation wavelength of 455 nm. The separation column used was two columns, Shodex® DM-614 (Showa Denko Co., Ltd.) connected in series.

2. Measurement of The SHMT Activity 0.1 ml of a 500 mM phosphate buffer solution (pH 7.3), 0.5 ml of a 1.0M glycine aqueous solution, 0.3 ml of 0.45% tetrahydrofolic acid solution (500 mM phosphate buffer solution (pH 7.3) containing 0.08% of formalin) and 0.2 ml of distilled water were placed in a 2.2 ml Eppendorf tube for pre-incubation at 50° C. for 5 minutes.

Next, 0.1 ml of the cell-treated solution (a solution diluted to 1:50 with use of a 50 mM phosphate buffer(pH 7.3) solution) was added to the solution and agitated, followed by reaction at 50° C. for 10 minutes. After completion of the reaction for a certain time, 0.3 ml of trichloroacetic acid (15% aqueous solution) was added to stop the reaction. The reaction solution was centrifugally separated and the resultant supernatant liquid was diluted to 1:5, followed by analysis of L-serine by HPLC. The analyzing conditions of L-serine by HPLC were as described above.

Experimental Example 2

The strain of Escherichia coli MT-10350 was cultivated in the same manner as in Experimental Example 1 and the culture solution was centrifugally separated to obtain wet cells. The thus-harvested cells were washed with a 0.85% NaCl aqueous solution in an amount of ⅓ of the culture solution, followed by centrifugal separation to collect washed cells. 88.8 g of the washed wet cells was added to a cooled 0.1M Tris. hydrochloride buffer solution (pH 7.5) to make a total of 800 g of a suspension. The resultant suspension was divided into two portions. One portion was subjected to breaking treatment with an ultrasonic disintegration (made by Branson Co., Ltd.) on ice. The resultant disrupted solution was further divided into two portions. The respective portions were charged into a container having a dissolved oxygen densitometer (Toa Denpa K.K.), an aeration nozzle, an agitator and a temperature controlling unit, to which Adekanol® LG-109 (made by Asahi Denka K.K.) was added for anti-foaming in an amount of 0.05%. Thereafter, the aeration amount was controlled so that the concentration of dissolved oxygen was as shown in Table 2 at 40° C., followed by measurement of initial SHMT and SD activities.

Four hours after the aeration, the respective activities were also measured with the residual rates being shown in Table 2. Another portion of the suspension was not subjected to the ultrasonic treatment and divided into further two portions. The respective portions were charged into a container having a dissolved oxygen densitometer (made by Toa Denpa K.K.), an aeration nozzle, an agitator and a temperature controlling unit, to which Adekanol® LG-109 (made by Asahi Denka K.K.) was added in an amount of 0.05% for anti-foaming. Thereafter, aeration was controlled so that the concentration of dissolved oxygen was as shown in Table 2. Four hours after the treatment, an equal amount of a 0.1M tris.hydrochloride buffer solution (pH=7.5) was added to the respective suspensions, followed by a breaking treatment on ice by the use of an ultrasonic breaking machine (made by Branson Co., Ltd.) to determine the SHMT and SD activities of the broken solutions.

Experimental Example 3

The strain of Escherichia coli MT-10350 (FERM P-7437) was cultivated in the same manner as in Experimental Example 1 and the culture solution was centrifugally separated to obtain wet cells. The thus obtained wet cells were washed with a 0.85% NaCl aqueous solution in an amount of ⅓ of the culture solution, followed by centrifugal separation to collect washed cells. 100 g of the washed wet cells was added to a 0.1M tris hydrochloride buffer solution (pH 7.5), cooled to 5° C., to make a total of 1000 g of a suspension. The resultant suspension was divided into five portions. The respective portions were charged into a container having a dissolved oxygen densitometer (Toa Denpa K.K.), an aeration nozzle, an agitator and a temperature controlling unit, to which Adekanol® LG-109 (made by Asahi Denka K.K.) was added for anti-foaming in an amount of 0.05%. Thereafter, the mixture was agitated for 4 hours under temperature conditions of 20° to 65° C. while keeping the dissolved oxygen at 5 ppm.

The SHMT and SD activities of the respective suspensions prior to the treatment and 4 hours after the treatment were measured with the residual rate being shown in Table 3.

TABLE 2

| | State of Cells | | | |
|---|---|---|---|---|
| | Cell-Disrupted Solution | | Cell Suspension | |
| | Concentration of Dissolved Oxygen | | | |
| Residual Rate (%): | 0 ppm | 5 ppm | 0 ppm | 5 ppm |
| SHMT Activity | | | | |
| 0 Hr. | 100 | 100 | 100 | 100 |
| 4 Hrs. | 102 | 106 | 100 | 100 |
| SD Activity | | | | |
| 0 Hr. | 100 | 100 | 100 | 100 |
| 4 Hrs. | 70 | 40 | 70 | 0 |

TABLE 3

| | Treating Temperature | | | | | |
|---|---|---|---|---|---|---|
| | 20° C. | 30° C. | 40° C. | 50° C. | 60° C. | 65° C. |
| Residual Rate of SHMT Activity (%): | | | | | | |
| 0 Hr. | 100 | 100 | 100 | 100 | 100 | 100 |
| 4 Hrs. | 100 | 100 | 100 | 75 | 40 | 0 |
| Residual Rate of SD Activity (%): | | | | | | |
| 0 Hr. | 100 | 100 | 100 | 100 | 100 | 100 |
| 4 Hrs. | 80 | 35 | 0 | 0 | 0 | 0 |

* The dissolved oxygen at the time of the treatment was controlled at 5 ppm.

Experimental Example 4

The strain of Escherichia coli MT-10350 was cultivated and collected in the same manner as in Experimental Example 2 to obtain 500 g of the washed wet cells. 1160 g of pure water was charged into a 2.6 liter mini-jar fermenter (having six turbine agitation blades and available from Marubishi Engi Co., Ltd.), followed by agitation (600 rpm) at 40° C. under aeration (1 vvm) whereupon the concentration of dissolved oxygen was determined with a value of 6.4 ppm. After the aeration was stopped, 200 g of the washed wet cells was added to 1160 g of the pure water, followed by gentle agitation (ca. 100 rpm) and continuous measurement of the concentration of dissolved oxygen in the suspension at 40° C. As a result, it was found that the concentration of dissolved oxygen quickly dropped to 0 ppm in 15 minutes. Separately, 1080 g of pure water was charged into the same mini-jar fermenter as above-mentioned, to which 300.4 g (4.00 mols) of glycine was added and dissolved under a gentle agitation at 40° C., followed by addition of 2.3 g of NaOH to adjust the pH to 7.5. Then, aeration (1 vvm) was carried out under agitation (600 rpm) to give rise to a saturated concentration of dissolved oxygen. 221.8 g of the washed wet cells was added to the resultant solution. 20 minutes after that, the concentration of dissolved oxygen in the solution was zero. A gentle agitation (100 rpm) was continued, without aeration, at 40° C. for 17 hours for the treatment with glycine and the thus-treated solution was subjected to measurement of the concentration of dissolved oxygen in about 150 g of the solution, with a value of 0 ppm. 3 liters/minute of air (2.0 vvm) were injected into 1500 g of the glycine-treated solution under agitation (400 rpm). At the time when the concentration of dissolved oxygen reached saturation (about 6.5 ppm), the injection of air was stopped. After it was stopped, the concentration of dissolved oxygen in the glycine-treated solution reached zero in about 10 minutes.

When air was continuously injected to a concentration of dissolved oxygen which was near saturation (6.5 ppm), the consumption of oxygen decreased with an increase of the air injecting time as shown in FIG. 1 wherein the consumption amount of oxygen immediately after the treatment with glycine was assumed as 100%.

It will be noted that the measurement of dissolved oxygen was effected using a dissolved oxygen indicator (of the galvanic electrode type, Model DY-2 available from Marubishi Engi Co., Ltd.).

EXAMPLE 1

The cells obtained by cultivating the strain of *Escherichia coli* MT-10350 according to the procedure set forth in Experimental Example 1 was collected by centrifugal separation. 40 g of the thus-obtained wet cells was added to a one liter flask equipped with a dissolved oxygen densitometer, a pH meter, an agitator, an aeration nozzle provided with a super jar and a temperature controlling unit in which a solution of 36 g of glycine dissolved in 125 g of distilled water with a pH adjusted to 7.5 had been placed. The mixture was gently agitated without aeration at 40° C. for 16 hours. Thereafter, the mixture was aerated at 40° C. for 4 hours while keeping the concentration of dissolved oxygen at a level of not less than 1 ppm.

200 g of the thus-aerated solution was added to a reaction solution obtained by mixing 340 g of glycine, 1.0 g of tetrahydrofolic acid and 20 mg of pyridoxal phosphate in 700 g of distilled water and previously prepared in a two liter reactor equipped with a pump for feeding formalin, a pH meter, an agitator and a temperature controlling unit.

After the addition of the aerated solution, the reaction solution was heated to 50° C. and its pH was adjusted to 6.7 by means of NaOH. Subsequently, while analyzing the concentration of formalin in the reaction solution, the reaction was carried out in such a way that the concentration of formalin in the reaction solution was within a tolerance range satisfying the following equation:

concentration of formalin (mM)=(20 mM)+(10 mM)×(reaction time).

On the other hand, the pit of the reaction solution was maintained at 6.6 by addition of 1N-NaOH. The reaction was performed for 35 hours. After completion of the reaction for the given time, the concentrations of L-serine and glycine in the reaction solution were determined by HPLC, with the result that 425 g of L-serine was found to be produced.

After completion of the reaction, sulfuric acid was added to the reaction solution to adjust the pH to 4.0, followed by addition of 21.3 g of active carbon (PMSX ®, available from Mitsui Pharm. Co., Ltd.), heating to 90° C. for 1 hour, and thermal filtration. The resultant filtrate was concentrated under reduced pressure to the half in amount of the reaction solution, followed by cooling for crystallization and filtration.

The crystals separated by filtration were dried to obtain 127.5 g of L-serine. The L-serine had a purity of 99.44% and an optical rotation of +15.2.

The above procedure was repeated using *Escherichia coli* MT-10351, with the results shown in Table 4.

TABLE 4

| Results of The Reaction | Strains | |
|---|---|---|
|  | MT-10350 | MT-10351 |
| total amino acid balance | 99.3 | 99.0 |
| yield based on formalin (%) | 93.0 | 93.8 |
| selectivity to serine (%) | 100.0 | 99.5 |

Yield based on formalin: produced L-serine (mols)/consumed formalin (mols)

Selectivity to serine: purified L-serine (mols)/consumed glycine (mols)

EXAMPLE 2

*Escherichia coli* MT-10350 was cultivated and the resultant cells were collected in the same manner as in Experimental Example 2, followed by suspending the washed wet cells in distilled water at a concentration of the cells of 2.5% (wt % based on the dried cells) and adjusting the pH to 7.5 by the use of NaOH. Thereafter, the suspension was aerated under agitation at 40° C. for 4 hours while keeping the concentration of dissolved oxygen at 1 to 4 ppm. The cells were broken into finer pieces by means of an ultrasonic disruptor and subjected to measurement of the SHMT activity, with the result that the SHMT activity was 200 U/ml. 375 g of glycine, 1.00 g of tetrahydrofolic acid and 20 mg of pyridoxal phosphate were added to 700 g of distilled water, followed by adjustment of the pH to 6.7 by the use of NaOH and heating to 50° C. The resultant substrate solution was charged into a light-shielded 2 liter flask provided with a pH meter, an agitator, an N$_2$ gas blowing nozzle, a pump for feeding formalin and a temperature controlling unit.

After addition of 250 g of the cell-broken, aerated solution, a formalin aqueous solution was intermittently added by means of the feed pump. Formalin was added at such a rate that while the concentration of the formalin in the reaction solution was analyzed, the concentration of the formalin was controlled in the same manner as in Example 1.

The pH of the reaction solution was maintained at 6.6 by addition of a 2N NaOH aqueous solution. The reaction time was 35 hours. After completion of the reaction, the concentrations of L-serine and glycine in the reaction solution were analyzed by HPLC, revealing that 410.0 g of L-serine was produced. The results of the reaction are shown in Table 5.

The above procedure was repeated using *Escherichia coli* MT-10351, with the results shown in Table 5.

TABLE 5

| | Strain | |
|---|---|---|
| | MT-10350 | MT-10351 |
| total amino acid balance | 99.7 | 98.6 |
| yield based on formalin (%) | 93.6 | 92.1 |
| selectivity to serine (%) | 99.1 | 97.8 |

Comparative Example 1

The strain of *Escherichia coli* MT-10350 was cultivated and the resultant cells were collected by centrifugal separation in the same manner as in Experimental Example 1. 40 g of the resultant wet cells was added to a solution, which was obtained by dissolving 36 g of glycine in 125 g of distilled water and adjusted in pH to 7.5, in a one liter flask equipped with a dissolved oxygen densitometer, a pH meter, an agitator, an aeration nozzle with a super jar and a temperature regulator. The solution was gently agitated at 40° C. for 20 hours without aeration. Subsequently, 340 g of glycine, 1.0 g of tetrahydrofolic acid, 20 mg of pyridoxal phosphate and 700 g of distilled water were placed in a two liter reactor, which was subsequently equipped with a pump for formalin, a pH meter, an agitator and a temperature regulator, followed by addition of 200 g of the non-aerated solution. The reaction solution was heated to 50° C. and the pH was adjusted by means of NaOH to 6.7. Thereafter, while the concentration of formalin in the reaction solution was analyzed, the reaction was carried out so that the concentration of formalin in the reaction solution was controlled to be not higher than a range satisfying the following equation: {(concentration of formalin mM)=(20 mM)+(10 mM)×(reaction time)}. On the other hand, the pH of the reaction solution was maintained at 6.6 by addition of 1N NaOH. The reaction was continued for 35 hours. After the reaction over the predetermined time, the concentrations of L-serine and glycine in the reaction solution were analyzed by HPLC, revealing that 245.6 g of L-serine was produced. The results are shown in Table 6.

TABLE 6

| | Strain MT-10350 |
|---|---|
| total amino acid balance | 89.9 |
| yield based on formalin (%) | 74.6 |
| selectivity to serine (%) | 78.4 |

Comparative Example 2

The general procedure of Comparative Example 2 was repeated except that the pH adjustment was made using a 2M-KOH aqueous solution. The results of the reaction are shown in Table 7.

TABLE 7

Results of the Reaction

| | Strain MT-10350 pH controlling agent 2M KOH |
|---|---|
| total amino acid balance | 87.6 |
| yield based on formalin (%) | 96.1 |
| selectivity to serine (%) | 81.6 |

Comparative Example 3

*Escherichia coli* MT-10350 was cultivated and the resultant cells were collected in the same manner as in Experimental Example 2, followed by suspending the wet cells in distilled water at a concentration of the cells of 2.5% (wt % based on the dried cells) and adjusting the pH to 7.5 by the use of NaOH. Thereafter, the suspension was passed with $N_2$ so that the concentration of dissolved oxygen was 0 ppm and was thus aerated under agitation at 40° C. for 4 hours. The cells were broken into finer pieces by means of an ultrasonic wave breaking machine and subjected to measurement of the SHMT activity, with the result that the SHMT activity was 200 U/ml. 375 g of glycine, 1.00 g of tetrahydrofolic acid and 20 mg of pyridoxal phosphate were added to 700 g of distilled water, followed by adjustment of the pH to 6.7 by the use of NaOH and heating to 50° C. The resultant substrate solution was charged into a light-shielded 2 liter flask provided with a pH meter, an agitator, an $N_2$ gas blowing nozzle, a pump for feeding formalin and temperature regulator, to which 250 g of the cell-broken aerated solution was added, followed by intermittently adding an aqueous formalin solution through the feed pump. The addition rate of the formalin was so controlled that while analyzing the concentration of formalin in the reaction solution, the concentration was controlled in the same manner as in Example 1. The pH adjustment of the reaction solution was made by addition of a 2N-NaOH aqueous solution to keep the pH at 6.6. The reaction was continued over 35 hours, after which the concentrations of L-serine and glycine in the reaction solution were analyzed by HPLC, revealing that 222.4 g of L-serine was produced. The results are summarized in Table 8.

TABLE 8

Results of the Reaction

| | Strain MT-10350 pH controlling agent 2M KOH |
|---|---|
| total amino acid balance | 86.3 |
| yield based on formalin (%) | 79.3 |
| selectivity to serine (%) | 75.5 |

What is claimed is:

1. In a process of preparing L-serine from glycine and formaldehyde in the presence of a harvested microorganism or the cell extract thereof having a serine hydroxymethyl transferase activity, the improvement which comprises pretreating *Escherichia coli* MT-10350 FERM BP-793, *Escherichia coli* MT-10351 FERM BP-794 or the cell extract of either of the *Escherichia coli* strains in a suspension or solution form, under conditions of dissolved oxygen of 1 ppm or more and a temperature of 60° C. or less prior to the addition of the reaction mixture.

2. The process of preparing L-serine according to claim 1, wherein the temperature of 60° C. or less in the pre-treatment is 30° to 50° C.

3. The process of preparing L-serine according to claim 1, wherein the dissolved oxygen of 1 ppm or more in the pre-treatment is attained by passing air or oxygen through the suspension or solution.

4. The process of preparing L-serine according to claim 1, wherein the pre-treatment is carried out while agitating the suspension or solution.

5. The process of preparing L-serine according to claim 1, wherein the pre-treatment is carried out for 2 to 10 hours.

6. The process of preparing L-serine according to claim 1, wherein the pre-treatment is carried out at pH 6 to 9.

7. The process of preparing L-serine according to claim 1, wherein the pre-treatment is carried out in the presence of an anti-foaming agent.

8. The process of preparing L-serine according to claim 1, wherein the pre-treatment is carried out in the presence of glycine.

9. The process of preparing L-serine according to claim 1, wherein the formaldehyde is in a form selected from the group consisting of gas, aqueous solution, alcoholic solution and paraformaldehyde.

10. The process of preparing L-serine according to claim 1, wherein the glycine and the formaldehyde are reacted in the presence of a nitrogen gas or a reducing agent.

11. The process of preparing L-serine according to claim 1, wherein the glycine and the formaldehyde are reacted in a pH range of 6 to 9.

12. The process of preparing L-serine according to claim 1, wherein the glycine and the formaldehyde are reacted in a temperature range of 30° to 60° C.

13. The process of preparing L-serine according to claim 1, wherein the glycine and the formaldehyde are reacted for 20 to 30 hours.

* * * * *